United States Patent
McKnight et al.

(10) Patent No.: US 10,597,338 B2
(45) Date of Patent: *Mar. 24, 2020

(54) LIQUID FORMULATIONS OF UREASE INHIBITORS FOR FERTILIZERS

(71) Applicant: World Sources Enterprises, LLC, Charleston (KN)

(72) Inventors: Gary David McKnight, High Point, NC (US); David Bruce Parker, Canyon, TX (US); Yang Zehni, Ningbo (CN); Ray Perkins, Bakersville, NC (US); Wei Xu, Sugarland, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/294,002

(22) Filed: Mar. 6, 2019

(65) Prior Publication Data
US 2019/0202754 A1    Jul. 4, 2019

Related U.S. Application Data

(63) Continuation of application No. 15/792,288, filed on Oct. 24, 2017, now Pat. No. 10,329,208, which is a
(Continued)

(51) Int. Cl.
*C05G 3/08* (2006.01)
*C05C 9/02* (2006.01)
(Continued)

(52) U.S. Cl.
CPC .................. *C05G 3/08* (2013.01); *C05C 9/00* (2013.01); *C05C 9/005* (2013.01); *C05C 9/02* (2013.01);
(Continued)

(58) Field of Classification Search
CPC ....................................................... C05C 9/00
See application file for complete search history.

(56) References Cited

U.S. PATENT DOCUMENTS

| | | |
|---|---|---|
| 3,152,039 A | 10/1964 | Mattson |
| 3,353,949 A | 11/1967 | Nau |
| | (Continued) | |

FOREIGN PATENT DOCUMENTS

| | | |
|---|---|---|
| CN | 101200400 B | 6/2008 |
| GB | 1371694 A | 2/1972 |
| | (Continued) | |

OTHER PUBLICATIONS

Prosecution history of PCT Application No. PCT/US2013/40199.
(Continued)

*Primary Examiner* — Wayne A Langel
(74) *Attorney, Agent, or Firm* — Ben Schroeder Law, PLLC

(57) ABSTRACT

An improved solvent system for the formulation and application of N-alkyl thiophosphoric triamide urease inhibitors. These formulations provide safety and performance benefits relative to existing alternatives and enable storage, transport and subsequent coating or blending with urea based or organic based fertilizers. These formulations are comprised primarily of environmentally friendly aprotic and protic solvents (particularly dimethyl sulfoxide and alcohols/polyols) to stabilize the urease inhibitor.

20 Claims, 10 Drawing Sheets

Related U.S. Application Data continuation of application No. 15/636,211, filed on Jun. 28, 2017, now Pat. No. 10,301,231, which is a continuation of application No. 13/890,082, filed on May 8, 2013, now Pat. No. 9,732,008.

(60) Provisional application No. 61/708,105, filed on Oct. 1, 2012.

(51) Int. Cl.
| | |
|---|---|
| *C05C 9/00* | (2006.01) |
| *C05G 3/00* | (2020.01) |
| *C09K 15/28* | (2006.01) |
| *C07F 9/22* | (2006.01) |

(52) U.S. Cl.
CPC ......... *C05G 3/0041* (2013.01); *C05G 3/0064* (2013.01); *C07F 9/224* (2013.01); *C09K 15/28* (2013.01)

(56) References Cited

U.S. PATENT DOCUMENTS

| | | |
|---|---|---|
| 3,425,819 A | 2/1969 | Barry et al. |
| 3,961,932 A | 6/1976 | Miller |
| 3,986,859 A | 10/1976 | Molinet |
| 4,234,332 A | 11/1980 | Michaud |
| 4,294,604 A | 10/1981 | Evrard |
| 4,294,804 A | 10/1981 | Evrard |
| 4,530,714 A | 7/1985 | Kolc et al. |
| 4,943,307 A | 7/1990 | Detre et al. |
| 5,024,689 A | 6/1991 | Sutton et al. |
| 5,071,463 A | 12/1991 | Narayanan et al. |
| 5,106,984 A | 4/1992 | Haplen |
| 5,160,528 A | 11/1992 | Chaudhuri et al. |
| 5,352,265 A | 10/1994 | Weston et al. |
| 5,354,726 A | 10/1994 | Narayanan et al. |
| 5,364,438 A | 11/1994 | Weston et al. |
| 5,435,821 A | 7/1995 | Duvdevani et al. |
| 5,698,003 A | 12/1997 | Omilinsky |
| 6,106,984 A | 8/2000 | Kato et al. |
| 6,262,183 B1 | 7/2001 | Domb et al. |
| 6,488,734 B1 | 12/2002 | Barth |
| 6,830,603 B2 | 12/2004 | Whitehurst et al. |
| 7,615,232 B2 | 11/2009 | Wurtz et al. |
| 3,048,189 A1 | 11/2011 | Whitehurst et al. |
| 8,048,189 B2 | 11/2011 | Whitehurst et al. |
| 8,133,294 B2 | 3/2012 | Whitehurst et al. |
| 3,562,711 A1 | 8/2013 | Sutton et al. |
| 8,562,711 B2 | 8/2013 | Sutton et al. |
| 9,056,804 B2 | 6/2015 | Phillip et al. |
| 9,732,008 B2 * | 8/2017 | McKnight ............ C05G 3/0041 |
| 10,221,108 B2 * | 3/2019 | McKnight ............ C05G 3/0041 |
| 10,301,231 B2 * | 5/2019 | McKnight ............ C05G 3/0041 |
| 10,329,208 B2 * | 6/2019 | McKnight ............ C05G 3/0041 |
| 2003/0211943 A1 | 11/2003 | Harwell |
| 2004/0163434 A1 | 8/2004 | Quin |
| 2006/0185411 A1 | 8/2006 | Hojjatie et al. |
| 2007/0077428 A1 | 4/2007 | Hamed et al. |
| 2007/0157689 A1* | 7/2007 | Sutton ...................... C05C 9/00 71/28 |
| 2007/0295047 A1 | 12/2007 | Sutton |
| 2008/0070871 A1 | 3/2008 | Hucke et al. |
| 2010/0206030 A1 | 8/2010 | Whitehurst et al. |
| 2010/0248334 A1 | 9/2010 | McDaniel |
| 2011/0015076 A1 | 1/2011 | Angst et al. |
| 2011/0154874 A1 | 6/2011 | Rahn et al. |
| 2011/0233171 A1 | 9/2011 | Cigler et al. |
| 2011/0233474 A1 | 9/2011 | Cigler et al. |
| 2011/0259068 A1 | 10/2011 | Whitehurst et al. |
| 2011/0314883 A1 | 12/2011 | Whitehurst et al. |
| 2013/0125321 A1 | 5/2013 | Newbould et al. |
| 2013/0252960 A1 | 9/2013 | Brewster et al. |
| 2014/0174140 A1* | 6/2014 | Ortiz-Suarez ............ C05G 3/08 71/27 |

FOREIGN PATENT DOCUMENTS

| | | |
|---|---|---|
| NZ | 586790 A | 6/2012 |
| WO | 2005/075602 A1 | 8/2005 |
| WO | 2008/000196 | 1/2008 |
| WO | 2013/071344 | 5/2013 |
| WO | 2013/090324 | 6/2013 |

OTHER PUBLICATIONS

International Search Report for PCT/US2013/40199 dated Oct. 24, 2015.
New Zealand Office Action for IP No. 706137 dated Oct. 6, 2015.
International Preliminary Report on Patentability for PCT/US2013/40199 dated Apr. 7, 2015.
Written Opinion of the International Searching Authority for PCT/US2013/40199 dated Oct. 24, 2015.
EP Search Report for EP Application No. 13844259.5 dated May 10, 2016.
Declaration of Willis I. Thornsberry dated Feb. 21, 1967.
Prosecution history of US Application No. PCT/US2014/67453.
Prosecution history of U.S. Appl. No. 13/890,082 and all references cited/considered therein.
International Search Report and Written Opinion for PCT/US2014/67453 dated Feb. 6, 2015 and references cited terein.
International Preliminary Report on Patentability for PCT/US2014/67453 dated May 31, 2016.
Volatilization losses from surface-applied urea during cold weather months / Dec. 13-14, 2011/ Rick Engel / Department of Land Resources and Environmental Sciences / Montana State University / Bozeman, MT 59717-31201 / Manitoba Agronomist Conference, Winnipeg, Manitoba.
N-(n-Butyl)thiophosphoric Triamide / Technical Data Sheet / Santa Cruz Biotech.
Arkema announces its new DMSO website at www.arkema.com/dmso Nov. 24, 2009—Press release.
Prosecution history of U.S. Appl. No. 15/636,211 and all references cited/considered therein.
Prosecution history of U.S. Appl. No. 15/792,288 and all references cited/considered therein.
Prosecution history of U.S. Appl. No. 15/793,326 and all references cited/considered therein.

* cited by examiner

LIQUID FORMULATIONS OF UREASE INHIBITORS FOR FERTILIZERS

The present application is a continuation and claims priority under 35 § USC 120 to U.S. application Ser. No. 15/792,288, filed Oct. 24, 2017, which in turn claims priority and is a continuation of U.S. application Ser. No. 15/636,211 filed Jun. 28, 2017, which in turn is a continuation and claims priority to U.S. application Ser. No. 13/890,082 filed May 8, 2013, which in turn claims priority under 35 § USC 119(e) to U.S. Provisional Application 61/708,105 filed Oct. 1, 2012, the entire contents of all of which are hereby incorporated by reference in their entireties.

FIELD OF THE INVENTION

In embodiments, the present invention relates to improved solvent formulations for the urease inhibitor N-(n-butyl) thiophosphoric triamide, hereafter referred to by its acronym NBPT. NBPT is a solid chemical substance, which is dissolved in a suitable solvent to allow application at low levels in the field. Additionally, solutions of NBPT are desirable when it is to be incorporated as a component of a granular mixed fertilizer, such that it can be deposited as a coating in a controlled and homogenous layer. In one embodiment, this invention proposes formulations of mixtures containing aprotic and protic solvents which are more environmentally friendly and are safer for workers to handle than known NBPT solutions. Moreover, performance advantages relative to NBPT solution stability, solution handling, and loading levels are disclosed for these new formulations.

BACKGROUND OF THE INVENTION

Description of the Prior Art

Nitrogen is an essential plant nutrient and is thought to be important for the adequate and strong foliage. Urea provides a large nitrogen content and is one of the best of all nitrogenous fertilizer materials, which consequently makes it an efficient fertilizer compound. In the presence of soil moisture, natural or synthetic ureas are converted to ammonium ion, which is then available for plant uptake. When applied as a fertilizer material, native soil bacteria enzymatically convert urea to two molar equivalents of ammonium ion for each mole of urea as demonstrated by the following two reactions:

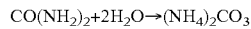
$$CO(NH_2)_2 + 2H_2O \rightarrow (NH_4)_2CO_3$$

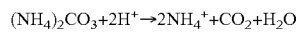
$$(NH_4)_2CO_3 + 2H^+ \rightarrow 2NH_4^+ + CO_2 + H_2O$$

In the presence of water, the ammonium thus produced is in equilibrium with ammonia. The equilibrium between $NH_4^+$ and $NH_3$ is pH dependent, in accordance with the following equilibrium:

$$NH_4^+ + OH^- \leftrightarrow NH_{3(solution)} + H_2O$$

As such, gaseous ammonia losses are higher at higher pH values. The flux of $NH_3$ from soil is primarily dependent on the $NH_3$ concentration, pH, and temperature. In the presence of oxygen, ammonium can also be converted to nitrate ($NO_3^-$). Nitrogen in both its ammonium and nitrate forms may then be taken up as nutrient substances by growing plants.

The ammonium ion can also ultimately be converted to ammonia gas, which escapes to the air. The concentrations of $NH_3$ in the air and in solution are governed by Henry's law constant (H), which is a function of temperature:

$$[NH_{3(air)}] = H[NH_{3(solution)}]$$

Urea fertilizer is often just applied once at the beginning of the growing season. A weakness in this nitrogen delivery system involves the different rates at which ammonium and nitrate are produced in the soil, and the rate at which ammonium and nitrate are required by the plant during its growing season. The generation of ammonium and nitrate is fast relative to its uptake by plants, allowing a considerable amount of the fertilizer nitrogen to go unutilized or to be lost to the atmosphere as ammonia gas, where it is no longer available to the plant. Thus, there is a desire to control the hydrolysis of urea to ammonium and ammonia gas, thereby making the urea fertilizer more effective for plant growth.

Numerous methods have been developed for making urea fertilizers more effective, and for controlling the volatilization of ammonia from urea. Weston et al. (U.S. Pat. No. 5,352,265) details a method for controlling urea fertilizer losses, including: (1) multiple fertilizer treatments in the field, staged across the growing season, (2) the development of 'controlled release' granular fertilizer products, using protective coatings which erode slowly to introduce the urea to the soil in a controlled fashion, and (3) the discovery of simple chemical compounds (urease inhibitors) which inhibit the rate at which urea is metabolized by soil bacteria and converted to the ammonium ion.

Use of various urea coatings to provide urea in a controlled fashion to the plant has been widely demonstrated. Phosphate coatings for urea have been described by Barry et al. (U.S. Pat. No. 3,425,819) wherein the coating is applied to urea as an aqueous phosphate mixture. Miller (U.S. Pat. No. 3,961,932) describes the use of chelated micronutrients to coat fertilizer materials. Polymer coatings have also been disclosed which control the delivery of fertilizer materials (see, for example, U.S. Pat. Nos. 6,262,183 and 5,435,821).

Whitehurst et al. (U.S. Pat. No. 6,830,603) teach the use of borate salts to produce coated urea fertilizer, as a means of controlling ammonia losses during the growth cycle. Whitehurst summarizes numerous examples of this coating strategy to inhibit the loss of ammonia nitrogen in the soil. Accordingly, the prior art considers the merits of coated fertilizer products as one means of inhibiting the loss of ammonia nitrogen in the soil. Urease inhibiting materials other than NBPT have been disclosed. Some examples include the use of polysulfide and thiosulfate salts as taught by Hojjatie et al (US 2006/0185411 A1) and the use of dicyandiamide (DCD) and nitrapyrin.

Kolc at al. (U.S. Pat. No. 4,530,714) teach the use of aliphatic phosphoric triamide urease inhibitors, including the use of NBPT for this purpose. Kolc mentions the use of aqueous and organic carrier media, but specifies volatile (and flammable) solvents from the group including acetone, diisobutylketone, methanol, ethanol, diethyl ether, toluene, methylene chloride, chlorobenzene, and petroleum distillates. The principle reason for the use of these solvents was to assure that negligible amounts of solvent residue be retained on the crop.

Improved carrier systems for NBPT have been described subsequent to the Kolc. NBPT is both a hydrolytically and thermally unstable substance and several solvent systems have been developed to overcome these and other weaknesses. Unfortunately, the existing formulations are problematic in their own right due to thermal stability concerns and the toxicity of key formulation components.

Generally, it is desirable that solvents being used in conjunction with fertilizers be water soluble in all proportions which allows for facile dispersion at the point of use as well as a relatively high flashpoint (so that it has a reduced chances of explosions and/or fires at elevated temperatures). Many of the formulation solvents disclosed in U.S. Pat. No. 4,530,714 do not possess these desirable properties. Examples of such problematic solvents from this patent include the use of toluene, a flammable and water immiscible solvent.

Weston et al. (U.S. Pat. No. 5,352,265) disclose the use of pyrrolidone solvents, such as N-Methyl pyrrolidone (NMP), as does Narayanan et al. (U.S. Pat. Nos. 5,160,528 and 5,071,463). It is shown that a solvents of this type can dissolve high levels of NBPT to produce product concentrates and that the resulting concentrates have good temperature stability. These features are useful in that they allow commercial products to be stored, pumped, and transported in conventional ways.

In U.S. Pat. No. 5,698,003, Omilinsky and coworkers also disclose the use of 'liquid amides" such as NMP in NBPT formulations. Omilinsky further speaks to the importance of solution stability and develops glycol-type solvents as desirable base solvents for NBPT delivery mixtures. The dominant role played by a liquid amide co-solvent is to depress the pour point of the mixture, which is insufficiently high as a consequence of the natural viscosity of glycols at reduced temperatures. NMP plays several roles in NBPT-based agrichemical formulations. As taught in '265, '528, and '463, NMP is a useful solvent capable of producing concentrated NBPT product formulations which have good temperature stability. It may also be used as an additive to depress the pour point of viscous base solvents, such as propylene glycol. Omilinsky discloses the use of NMP as a co-solvent to depress the pour point of propylene glycol in '003.

In mixtures such as those described in U.S. Pat. No. 5,698,003, the requirement for an additive to depress the pour point of glycol-type NBPT solvent formulations is described. Solvents such as propylene glycol have the attractive feature of being essentially nontoxic and are thus an attractive mixture component in agrichemical and pharmaceutical products. One drawback of some glycols is a relatively high viscosity level, which can make these materials resistant to flow and difficult to pour. Indeed, the dynamic viscosity at 25° C. of propylene glycol is 48.8 centipoise, almost 50 times that of water at the same temperature. Viscosity data for propylene glycol can be found in *Glycols* (Curme and Johnston, Reinhold Publishing Corp., New York, 1952). Omilinsky '003 describes the use of NMP as an additive capable of depressing the pour point of NBPT mixtures.

Although NMP and other liquid amide solvents play useful roles in the described NBPT formulations, concerns about the safety of these solvents has increased greatly in recent years. In particular, European Directives 67/548/EEC and/or 99/45/EC have recently classified N-methylpyrrolidone (NMP) as a reproductive toxin (R61) in amounts exceeding 5% of the product formulation. It is scheduled for listing on the European Union's 'Solvent of Very High Concern' list, which would preclude its use in industrial and agrichemical formulations. In the US, NMP is subject to California Proposition 65 (The Safe Drinking Water and Toxic Enforcement Act of 1986) requirements, which regulate substances known by the US State of California to cause cancer or reproductive harm.

Nothing in the prior art addresses the suitability of NMP in these formulations from the standpoint of safety, or proposes appropriate alternatives from the perspectives of both safety and performance.

Indeed, guidelines for the use of reaction solvents in the pharmaceutical industry also speak to the relatively poor safety profile of NMP. As reaction solvents may be present at residual levels in finished drug products such considerations are warranted. The International Conference on Harmonization of Technical Requirements for Registration of Pharmaceuticals for Human Use (ICH) classifies NMP as a 'solvent to be limited (Class 2)' in its document *Impurities: Guideline for Residual Solvents Q3C (R3)*.

NMP is potentially toxic if it is given directly to humans and/or animals. Moreover, it is possible that NMP may be toxic when it is ingested by higher order animals after passage through the food chain. For example, often times, fertilizers are not completely absorbed/used by fields/crops/plants on which they are used and the fertilizers end up in water-ways (such as fresh water, brackish water or salt water bodies). In those situations where at least a part of the fertilizer ends up in these bodies of water, they may be absorbed, ingested or otherwise taken in by organisms that are either directly or indirectly consumed by higher animals (such as humans). In these instances, it is possible that the fertilizer and/or compounds that are associated with said fertilizer may be directly and/or indirectly ingested by humans or higher animals and lead to toxicity to said humans. It is also possible that the fertilizers that end up in water ways may be directly ingested by higher animals/humans that drink the water.

Moreover, when toxic compounds that are associated with various fertilizers are used, not only may they be toxic to the higher animals but they also may be toxic to the animals lower in the food chain. At higher doses, this may mean die-off of the animals lower in the food chain, which consequently means that there may be economic consequences such as crop and/or animal die-off, which means lower profit margins and less food available.

In light of the above, it is desirable to develop formulations/fertilizers that are less toxic to the environment and to animals and humans.

An important feature of NBPT-based agrichemical formulation is their chemical stability in solution. Although such products are diluted with water at the point of use, NBPT undergoes hydrolysis in the presence of water. Aqueous solutions or emulsions of NBPT are therefore not practical from a commercial perspective and organic solvents are preferred as vehicles to deliver concentrated NBPT products. But NBPT is not chemically inert to all solvents, and its stability must be assessed in order to develop a product suitable to the needs of agrichemical users.

The stability of NBPT to NMP has been previously established in U.S. Pat. No. 5,352,265 (Weston et al.) and by Narayanan et al. (U.S. Pat. Nos. 5,160,528 and 5,071,463).

Beyond the consideration of NBPT chemical stability in the presence of formulation solvents is the inherent stability of the solvents themselves to hydrolysis. As NBPT products are often ultimately dispersed into water, the hydrolytic stability of liquid amide solvents like NMP is a consideration.

At elevated temperatures and pH levels, NMP hydrolysis can be significant ("M-Pyrrol" product bulletin, International Specialty Products, p. 48).

SUMMARY OF THE INVENTION

In one embodiment, the present invention relates to liquid formulations containing N-(n-butyl) thiophosphoric triamide (NBPT). In an embodiment, the formulations can be made by dissolving the NBPT into an aprotic solvent consisting of a) dimethyl sulfoxide, b) dialkyl, diaryl, or alkylaryl sulfoxide having the formula $R_1$—SO—$R_2$, when $R_1$ is methyl, ethyl, n-propyl, phenyl or benzyl and $R_2$ is ethyl, n-propyl, phenyl or benzyl, c) sulfolane, d) ethylene carbonate, propylene carbonate, or mixtures thereof. In an embodiment, these formulations can be mixed with a protic component consisting of 1) an alcohol or polyol from the family of alkylene and poly(alkylene) glycols (PG), 2) an alkylene glycol from the group comprised of ethylene, propylene, or butylene glycol, 3) glycerin, 4) an alkanolamine from the group comprising ethanolamine, diethanolamine, dipropanolamine, methyl diethanolamine, monoisopropanolamine and triethanolamine, and/or 5) ethyl, propyl, or butyl lactate. In one embodiment, we propose the use of dimethyl sulfoxide (DMSO) as a replacement in NBPT-based agrichemical products for more toxic solvents such as, for N-methyl pyrrolidone.

DETAILED DESCRIPTION OF THE INVENTION

Figure 1:
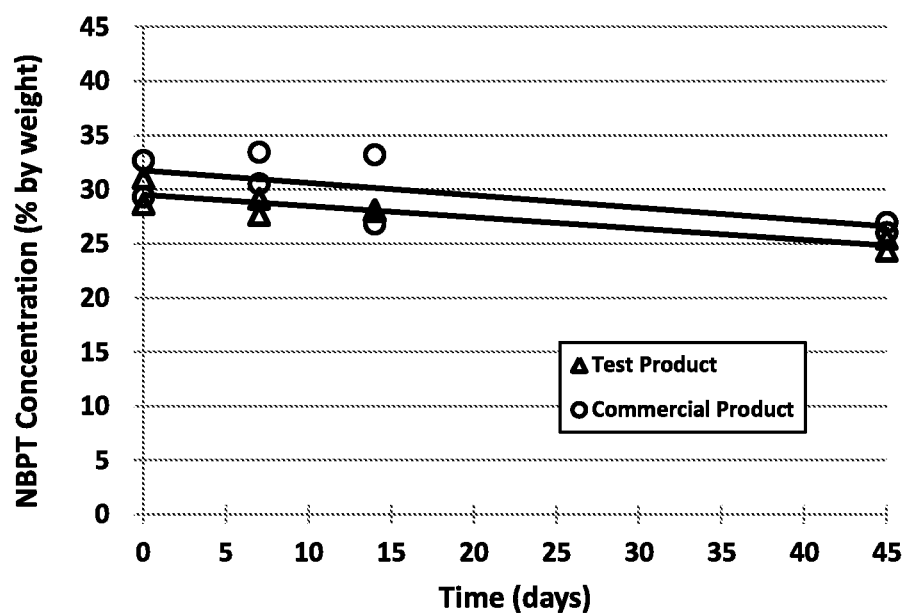
FIG. 1 shows accelerated chemical stability of NBPT solutions comparing the test product (50% PG, 25% DMSO, 25% NBPT) vs. the commercial product containing N-methyl pyrrolidone. The stability testing was conducted at 50° C., and concentrations were assayed by HPLC.

In an embodiment, the present invention relates to formulations containing N-(n-butyl) thiophosphoric triamide (NBPT). In an embodiment, these formulations are prepared by dissolving NBPT into an aprotic solvent consisting of a) dimethyl sulfoxide, b) dialkyl, diaryl, or alkylaryl sulfoxide having the formula $R_1$—SO—$R_2$, when $R_1$ is methyl, ethyl, n-propyl, phenyl or benzyl and $R_2$ is ethyl, n-propyl, phenyl or benzyl, c) sulfolane, d) ethylene carbonate, propylene carbonate, or mixtures thereof. In an embodiment, these formulations can be mixed with a protic component consisting of 1) an alcohol or polyol from the family of alkylene and poly(alkylene) glycols (PG), 2) an alkylene glycol from the group comprised of ethylene, propylene, or butylene glycol, 3) glycerin, 4) an alkanolamine from the group comprising ethanolamine, diethanolamine, dipropanolamine, methyl diethanolamine, monoisopropanolamine and triethanolamine, and/or 5) ethyl, propyl, or butyl lactate.

In one embodiment, dimethyl sulfoxide (DMSO) is used as a replacement in NBPT-based agrichemical products for more toxic solvents such as, for N-methyl pyrrolidone (NMP).

In one embodiment, the solution is either combined with a dry granular or liquid urea fertilizer and applied to cropland to make the fertilizer more effective for plant growth, and/or applied directly to urea-containing lands, surfaces, or products to reduce ammonia emissions.

In one embodiment, coated granular urea products containing additional plant nutrients can be prepared from granular urea, a source or sources of the additional nutrients in powdered form and the diluted NBPT containing mixture described below. Granular urea can be first dampened with the diluted NBPT containing mixture followed by mixing to distribute the NBPT containing liquid mixture over the granular urea surface using any commonly used equipment to commingle a liquid with a granular solid. After distribution of the diluted NBPT containing mixture over the granular surface, the additional nutrients in powdered form can be added to the dampened mixture and the resulting combined ingredients can be further mixed to distribute the powdered materials. In an alternate embodiment, the powdered materials may be first mixed with the granular urea and then the NBPT containing diluted mixture can be sprayed onto a tumbling bed of the dry ingredients to agglomerate the dry materials. This latter method may be particularly suited to continuous processing.

The term "urea fertilizer" as used herein refers to both natural and synthetic ureas, either used alone or mixed with other macro- and/or micronutrients and/or organic matter. Dry granular urea fertilizer contains about 46% nitrogen by weight.

In one embodiment, the compounds listed in this invention as aprotic and protic solvents may be described generally as sulfoxides and alcohols, respectively.

In an embodiment, the present invention relates to the use of safer and more environmentally friendly solvents to overcome the limitations of specific existing urease inhibitor formations. In an embodiment, the solvents used in the present invention are less toxic than the solvents that have been used in the prior art, for example, NMP.

In an embodiment, the formulations use combinations of polar aprotic solvents (sulfoxides, sulfones, dialkyl carbonates) with protic solvents (glycols, triols, and alkanolamines) to produce NBPT formulations having acceptable viscosity levels and high NBPT loading while also being relatively non-toxic. Moreover, in an embodiment, the protic/aprotic solvent mixtures demonstrate excellent NBPT stability as demonstrated by accelerated stability testing.

One aspect of the invention involves the use of dimethyl sulfoxide as a replacement for the more hazardous liquid amide component in formulations requiring such a co-solvent to modify the formulation's flow properties. In this aspect, this is a considerable improvement in light of increased regulatory scrutiny of the liquid amide solvents.

In one embodiment, the present invention relates to the use of DMSO with NBPT instead of NMP. NMP has a recognized reproductive toxicity and an examination of acute toxicity data shows that NMP is considerably more hazardous than dimethyl sulfoxide, by any exposure route. A summary of basic toxicological indicators is given in Table 1.

TABLE 1

Comparative acute/reproductive toxicity data for dimethyl sulfoxide and N-methyl pyrrolidone.

| Toxicological indicator | Dimethyl sulfoxide | N-methyl pyrrolidone |
|---|---|---|
| CAS | [67-68-4] | [872-50-4] |
| Oral LD-50 | 14,500-28,300 | 3,914 |
| Dermal LD-50 | 40,000 | 8,000 |
| Inhalation toxicity (MADL) | None established | 3200 µg/day |
| Reproductive toxin | no | yes |

MADL = Maximum Allowable Dosage Level per day (California Proposition 65)

As shown in the table above, it should be clear to those of ordinary skill in the art that DMSO is significantly less toxic than NMP. Furthermore, DMSO is classified as 'a solvent with low toxic potential (Class 3)'—the most favorable rating.

In one embodiment, the present invention addresses the shortcomings of solvents of the prior art by the use of specific mixtures of low toxicity polar aprotic solvents (most principally dimethyl sulfoxide) and various common protic solvents, that also tend to be relatively non-toxic.

In an embodiment, the present invention relates to formulations comprising aprotic/protic solvent mixtures that are used to fluidize the specific urease inhibitor N-(n-butyl) thiophosphoric triamide such that it might be used to coat fertilizer products.

In one embodiment, phosphate coatings for urea may be used wherein the coating is applied to urea as an aqueous phosphate mixture prior to adding the fertilizer additive of the present invention.

In an embodiment, chelated micronutrients may be used to coat fertilizer materials. Alternatively and/or additionally, polymer coatings may be used which control the delivery of fertilizer materials.

In one embodiment, the formulations of the present invention use DMSO as a solvent. DMSO has an advantage over prior art solvents such as NMP because DMSO does not undergo the hydrolysis that can be significant with NMP (see "M-Pyrrol" product bulletin, International Specialty Products, p. 48). Accordingly, when one uses DMSO, one has significantly more latitude in formulation development.

Further, the solvent properties of DMSO are useful in these formulations in that NBPT concentrations containing over 50 wt. % NBPT are attainable. Such high loading of an active substance by a solvent enables the manufacture of product concentrates, which can be less expensive to store, transport and use. When the fertilizer additive product arrives at the user, the user is able to dilute the concentrate with water and use the fertilizer additive (with fertilizer) for their crops/plants or the like.

In one embodiment, NBPT is dissolved into an aprotic solvent such as dimethyl sulfoxide. The NBPT-aprotic solvent solution may be used alone, or further mixed with a protic solvent to improve product handling, stability, and/or pourability of the solution.

The mixing of the materials may be accomplished in any commonly used method: for example; simply tank mixing materials prior to use, using a metering system to inject materials simultaneously, or mixing via a spray injection system.

In one embodiment, the NBPT/aprotic solvent/protic solvent mixture is mixed to produce a NBPT concentration of 5% to 75% by weight. Alternatively, a NBPT concentration of 5% to 60% by weight may be used. Alternatively, a NBPT concentration of 5% to 50% by weight may be used. Alternatively, a NBPT concentration of 5% to 40% by weight may be used. The initial solubilizing step in dimethyl sulfoxide can be accomplished between room temperature about 19° C. up to about 150° C. (the boiling point of DMSO at atmospheric pressure is ~190° C.). Alternatively, the solubilizing step in dimethyl sulfoxide can be accomplished between about 22° C. and up to 60° C.

The mixture can be mixed in any common mixing tank. Although the metering of NBPT, aprotic solvent, and protic solvent can be based on a weight, it may also be based on a volumetric basis.

A dye or colorant can be added to the mixture to aid in visual assessment of uniform coating during the coating of granular urea. Alternatively, a dye or colorant can be added to the mixture to aid in visual assessment of uniform coating during the coating of urea in aqueous mixtures just prior to application. In one embodiment, the colorant can include any nontoxic common food dye.

EXAMPLES

The following examples are provided to illustrate the practice of the invention. The examples are not intended to illustrate the complete range of possible uses. All compositions are based on mass percentages unless expressly stated. Concentrations of individual components are presented before their name. For example, 20.0% NBPT refers to a mixture containing 20.0% NBPT by weight.

Example 1

An NBPT solution was prepared by thoroughly mixing NBPT, DMSO, and PG to obtain the following percentages by weight: 50.0% PG, 30.0% DMSO, 20.0% NBPT.

Example 2

To test for the toxicity of DMSO and compare it to the relative toxicity of NMP, a 96 hr. acute toxicity range-finding test was conducted on juvenile crayfish (*Procambarus clarkii*) to estimate the lethal concentration to half of the population ($LC_{50}$) for the solution as described in example 1. Simultaneously, the $LC_{50}$ was determined on a commercially available NBPT solution which contained 26.7% NBPT by weight (per product label), and approximately 10% N-methyl pyrrolidone (MSDS range 10-30%), and approximately 63% propylene glycol (MSDS range 40-70%). Crayfish were placed into static chambers and exposed to equal NBPT concentrations of 0, 72, 145, 290, 580, and 1160 mg/L in clean water. The $LC_{50}$ of the solution of example 1 was 145 mg NBPT (as active ingredient)/L, while the $LC_{50}$ of Agrotain® Ultra was 75 mg NBPT (as active ingredient)/L. Because a higher $LC_{50}$ value indicates lower toxicity, the solution of example 1 was approximately half as toxic as the commercial product which contained N-methyl pyrrolidone.

This test demonstrates that the formulations of the present invention are significantly less toxic than the formulations of the prior art.

Example 3

NBPT solutions were prepared in DMSO and equal amounts of DMSO/PG to determine the maximum solubility at room temperature of 22° C. Following mixing and sonification, the samples were visually inspected, then filtered through a 0.45 µm filter and analyzed by near infrared reflectance spectrometry. At 22° C., the solubility of NBPT in DMSO was at least 58.9% by weight. The solubility of NBPT in equal amounts of DMSO/PG was at least 55.0% by weight.

It would be expected that at increased temperatures beyond that disclosed above, one might be able to increase the solubility of NBPT above the amounts found in this example providing an avenue for concentrates. Even if the temperature is lowered during transport, instructions on the use of the fertilizer additive may instruct the user to raise the temperature of the formulation to assure complete solubilization of the product prior to use.

Example 4

An NBPT solution was prepared by thoroughly mixing NBPT, DMSO, and PG to obtain the following percentages by weight: 50% PG, 25% DMSO, and 25% NBPT. The commercially available NBPT solution of example 2 was also used for comparison.

Example 5

The NBPT solutions of example 4 were placed into individual vials and incubated for 45 days at 50±1° C. in a laboratory oven. Samples were periodically removed for analysis of NBPT in solution using a Waters model 1525 High Performance Liquid Chromatograph (HPLC) equipped with a Waters 2489 tunable UV/visible detector. Suitable analytical parameters (mobile phase composition, column selection, etc.) such as would occur to workers knowledgeable in the art were employed, and raw data from the HPLC analyses were calibrated against authentic standards of NBPT having a nominal purity of >99%. FIG. 1 shows the results of the accelerated stability testing.

This test shows that the NBPT did not have significant deterioration at elevated temperatures meaning that the formulations of the present invention can be transported without worrying about significant degradation of the product.

Example 6

An NBPT solution was prepared by thoroughly mixing NBPT, DMSO, and PG to obtain the following percentages by weight: 35% PG, 40% DMSO, and 25% NBPT. The commercially available NBPT solution of example 2 was also used for comparison.

Example 7

Figure 2:
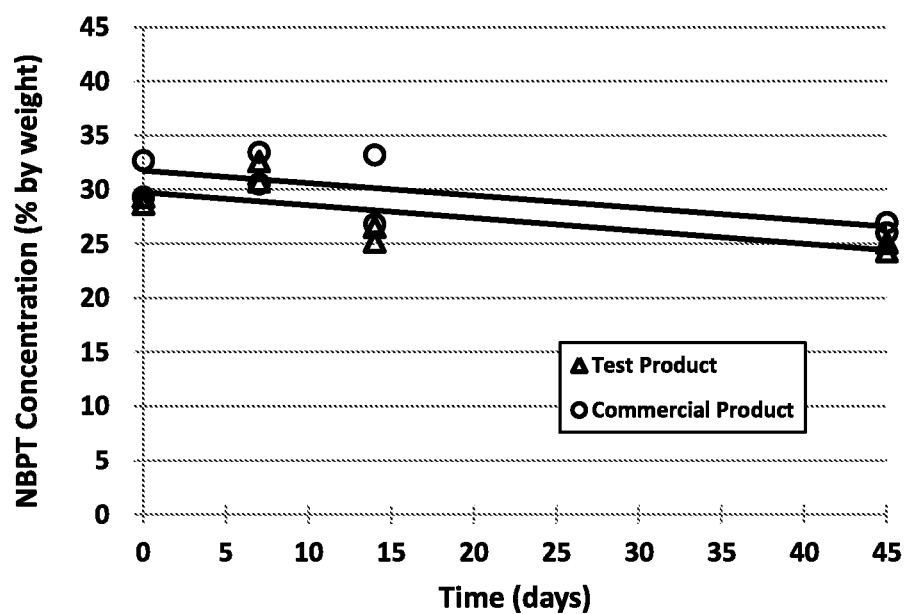
FIG. 2 shows accelerated chemical stability of NBPT solutions comparing the test product (35% PG, 40% DMSO, 25% NBPT) vs. the commercial product containing N-methyl pyrrolidone. The stability testing was conducted at 50° C., and concentrations were assayed by HPLC.

The NBPT solutions of example 6 were placed into individual vials and incubated for 45 days at 50±1° C. in a laboratory oven. Samples were periodically removed and analyzed using the procedures of example 5. FIG. 2 shows the results of the accelerated stability testing.

This test shows that the NBPT did not have significant deterioration at elevated temperatures when the relative amounts of DMSO are varied. Accordingly, the formulations of the present invention can be transported without worrying about significant degradation of the product at different DMSO levels.

Example 8

An NBPT solution was prepared by thoroughly mixing NBPT, DMSO, and PG to obtain the following percentages by weight: 20% PG, 40% DMSO, and 40% NBPT. The commercially available NBPT solution of example 2 was also used for comparison.

Example 9

Figure 3:
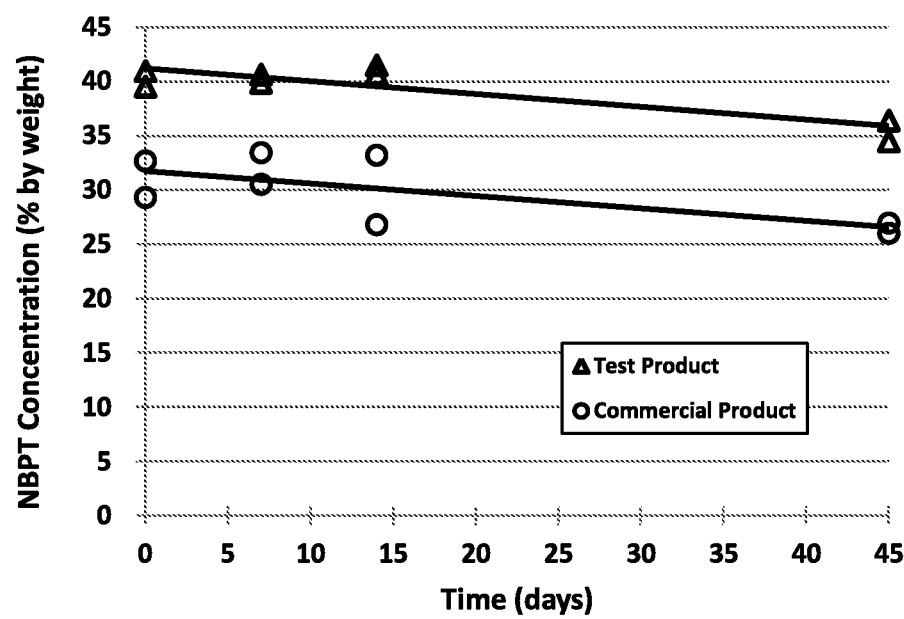
FIG. 3 shows accelerated chemical stability of NBPT solutions comparing the test product (20% PG, 40% DMSO, 40% NBPT) vs. the commercial product containing N-methyl pyrrolidone. The stability testing was conducted at 50° C., and concentrations were assayed by HPLC.

The NBPT solutions of example 8 were placed into individual vials and incubated for 45 days at 50±1° C. in a laboratory oven. Samples were periodically removed and analyzed using the procedures of example 5. FIG. 3 shows the results of the accelerated stability testing.

This test shows that the NBPT did not have significant deterioration at elevated temperatures when the relative amount of NBPT is increased. Accordingly, the formulations of the present invention can be transported without worrying about significant degradation of the product even at a relatively high NBPT concentration.

Example 10

An NBPT solution was prepared by thoroughly mixing NBPT, DMSO, glycerine, and methanol to obtain the following percentages by weight: 48.5% glycerine, 1.5% methanol, 25% DMSO, and 25% NBPT. The commercially available NBPT solution of example 2 was also used for comparison.

Example 11

Figure 4:
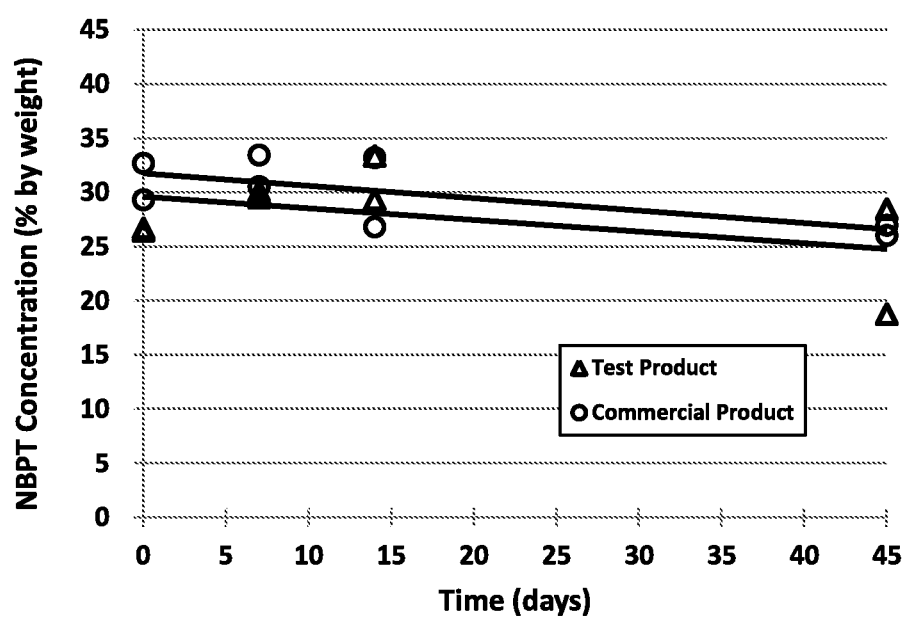
FIG. 4 shows accelerated chemical stability of NBPT solutions comparing the test product (48.5% glycerine, 1.5% methanol, 25% DMSO, 25% NBPT) vs. the commercial product containing N-methyl pyrrolidone. The stability testing was conducted at 50° C., and concentrations were assayed by FIG. 5 shows accelerated chemical stability of NBPT solutions comparing the test product (48.5% glycerine, 1.5% methanol, 25% DMSO, 25% NBPT) vs. the commercial product containing N-methyl pyrrolidone. The stability testing was conducted at 50° C., and concentrations were assayed by HPLC.

The NBPT solutions of example 10 were placed into individual vials and incubated for 45 days at 50±1° C. in a laboratory oven. Samples were periodically removed and analyzed using the procedures of example 5. FIG. 4 shows the results of the accelerated stability testing.

This test shows that the NBPT did not have significant deterioration at elevated temperatures with this formulation meaning that this formulation can be transported without worrying about significant degradation of the product.

Example 12

An NBPT solution was prepared by thoroughly mixing NBPT, DMSO, glycerine, and methanol to obtain the following percentages by weight: 33.5% glycerine, 1.5% methanol, 25% DMSO, and 40% NBPT. The commercially available NBPT solution of example 2 was also used for comparison.

Example 13

Figure 5:
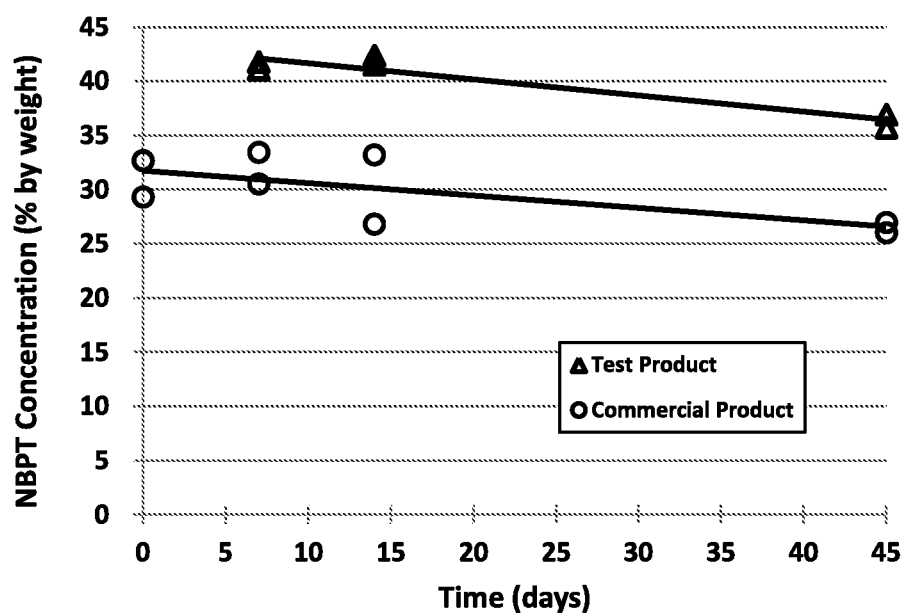

The NBPT solutions of example 12 were placed into individual vials and incubated for 45 days at 50±1° C. in a laboratory oven. Samples were periodically removed and analyzed using the procedures of example 5. FIG. 5 shows the results of the accelerated stability testing.

This test shows that the NBPT did not have significant deterioration at elevated temperatures with this formulation meaning that this formulation can be transported without worrying about significant degradation of the product.

Example 14

A buffer solution was prepared by carefully mixing monoisopropanolamine (MIPA) with glacial acetic acid (GAA) to obtain the following percentages by weight: 62.5% MIPA, 37.5% GAA. The mixing was conducted such that the temperature of the mixture remained below 50° C. Multiple NBPT solutions were prepared to obtain the following percentages by weight:
Mix A: 75% N-methyl pyrrolidone, 25% NBPT; Mix B: 75% PG, 25% NBPT; Mix C: 75% Buffer Solution, 25% NBPT; Mix D: 75% DMSO, 25% NBPT.

Example 15

Figure 6:
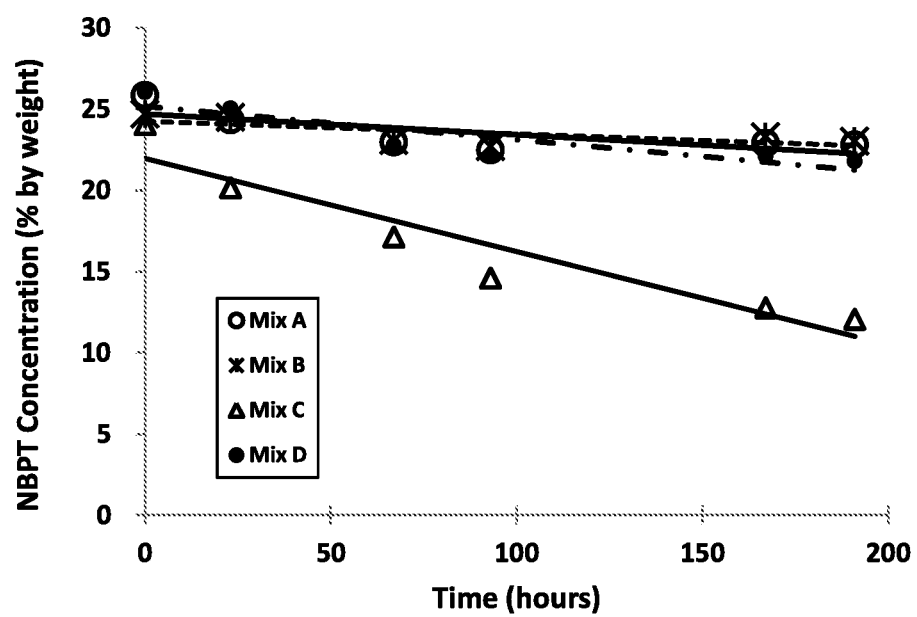
FIG. 6 shows accelerated chemical stability of four NBPT solutions: Mix A; 75.0% N-methyl pyrrolidone, 25% NBPT. Mix B; 75 PG, 25% NBPT. Mix C; 75.0% Buffered mix, 25.0% NBPT. Mix D; 75% DMSO, 25.0% NBPT. The stability testing was conducted at 50° C., and concentrations were assayed by HPLC.

The four NBPT solutions of example 14 were placed into individual vials and incubated for approximately 200 hrs. at 50±1° C. Samples were periodically removed and analyzed using the HPLC procedures of example 5. FIG. 6 shows the results of the accelerated stability testing.

This test shows that Mix C had more sample degradation at elevated temperatures than mixtures containing DMSO (Mix D), NMP (Mix A) or PG (Mix B). It should be noted that PG does not have the pourability of DMSO and NMP is more toxic than DMSO.

Example 16

Figure 7:
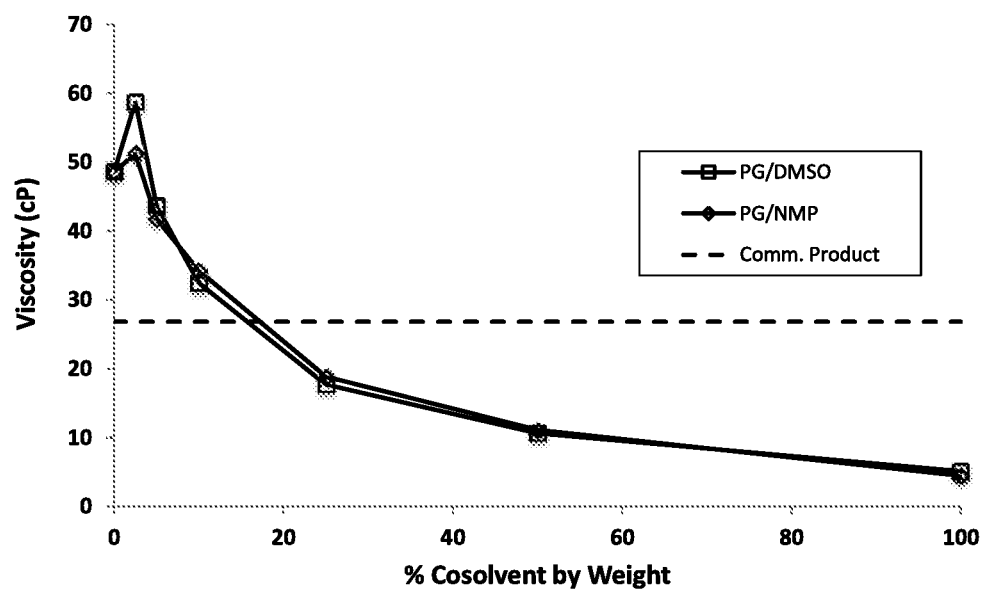
FIG. 7 shows viscosity testing results comparing mixtures of propylene glycol with varying percentages of co-solvents DMSO vs. NMP. Viscosities were measured using a Brookfield LVDV-E digital rotational viscometer with LVDV-E spindle set. Also shown is the viscosity of the commercial NBPT product, which contains NMP and PG, of example 2.
Figure 8:
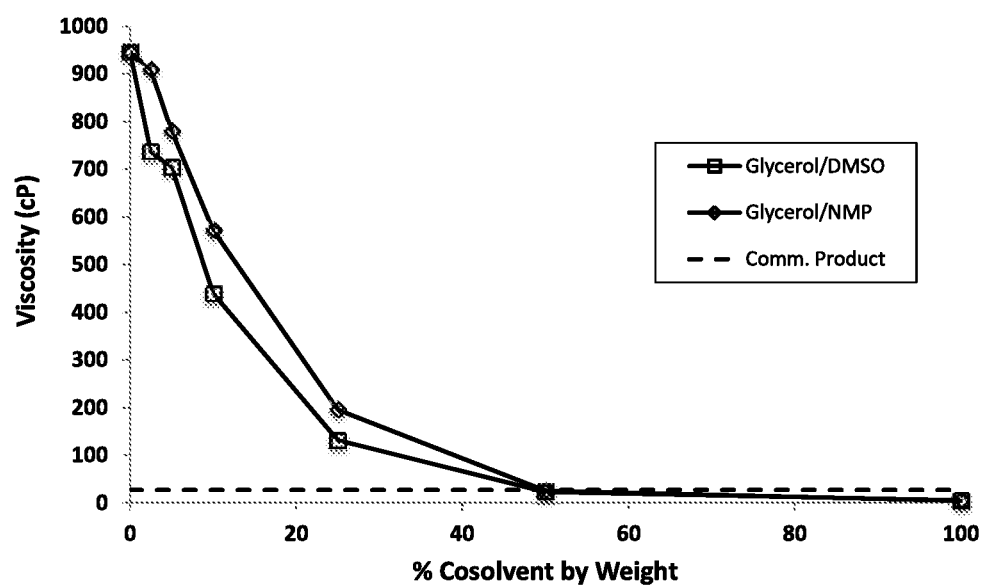
FIG. 8 shows viscosity testing results comparing mixtures of glycerol with varying percentages of co-solvents DMSO vs. NMP. Viscosities were measured using a Brookfield LVDV-E digital rotational viscometer with LVDV-E spindle set. Also shown is the viscosity of the commercial NBPT product, which contains NMP and PG, of example 2.
Figure 9:
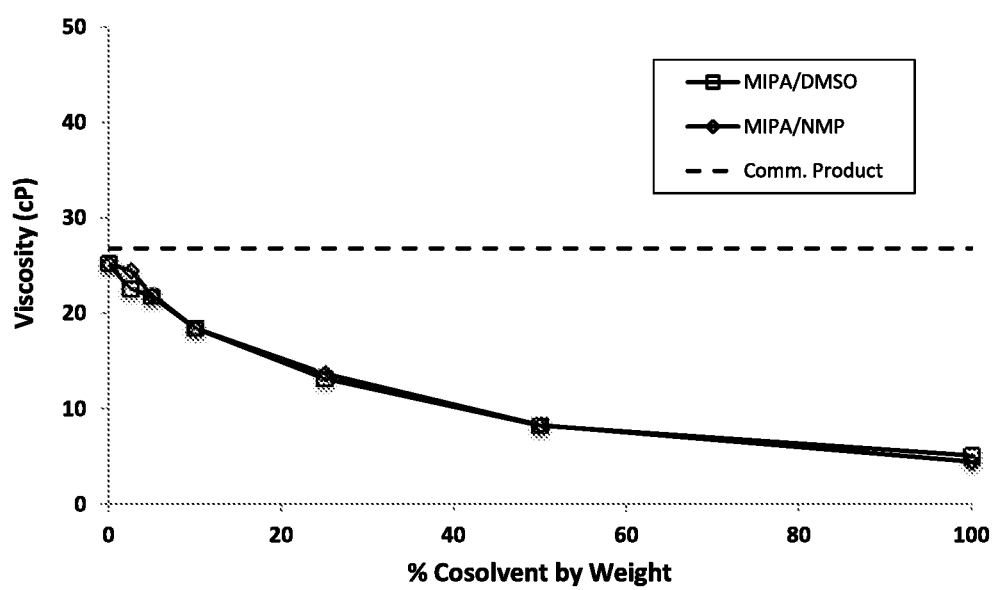
FIG. 9 shows viscosity testing results comparing mixtures of monoisopropanolamine (MIPA) with varying percentages of co-solvents DMSO vs. NMP. Viscosities were measured using a Brookfield LVDV-E digital rotational viscometer with LVDV-E spindle set. Also shown is the viscosity of the commercial NBPT product, which contains NMP and PG, of example 2.

Dynamic viscosity measurements were collected for propylene glycol, glycerin, and a representative alkanolamine (monoisopropanolamine, MIPA) with increasing levels of DMSO and NMP. A Brookfield LVDV-E digital rotational viscometer with LVDV-E spindle set (Brookfield Engineering Labs, Inc., Middleboro, Mass.) was employed for this work and was calibrated using Cannon N14 general purpose, synthetic base oil viscosity calibration standard solution (Cannon Instrument Company, State College, Pa.). The sampling was conducted at 21° C. FIGS. 7, 8, and 9 display the ability of DMSO to depress the viscosity of NBPT mixtures at 21° C. as a function of concentration, relative to similar NMP measurements.

This test shows that there is virtually no difference between DMSO and NMP in reducing the viscosity of various viscous formulations.

Example 17

A dye solution was added to the solution of example 1. 454 grams of granular urea was added to two clean, dry glass 2000 mL media bottles. Using a pipette, 1.87 mL, to represent application rate of 2 quarts product/ton urea of the dyed solution in example 1, was added to the urea in one of the bottles. Using a pipette, 1.87 mL, to represent application rate of 2 quarts product/ton urea of the commercial solution of example 2, was added to the urea in the other bottle. With the lid on, the media bottles were rotated hand over hand (1 rotation=360-degree hand over hand turn) until the urea was consistently coated. More complete coverage was observed after four turns in the dyed solution of example 1. The number of rotations required to obtain 100% visual coverage was recorded. The dyed solution of example 1 required 30 rotations for complete coverage, while the commercial product of example 2 required 35 rotations.

This test shows that formulations containing DMSO and a dye can more easily cover urea than a corresponding solution containing NMP and a dye.

Example 18

The NBPT solutions of examples 4, 6, 8, 10, and 12, together with the commercial NBPT solution of example 2, were placed in a −20° C. freezer for 48 hrs. The NBPT solutions of examples 4, 6, 8, and the commercial NBPT solution of example 2, were all freely flowable at −20° C. The NBPT solution of example 10 was very viscous but still flowable. The NBPT solution of example 12 was a solid at −20° C.

Example 19

Figure 10:
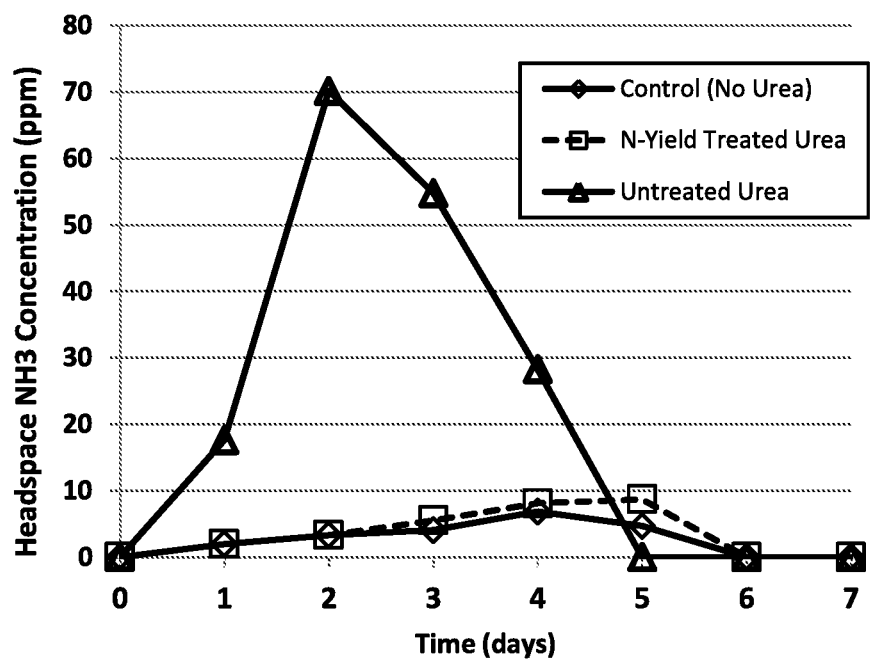
FIG. 10 shows ammonia emissions testing results from soil which had been applied commercial urea fertilizer vs. commercial urea fertilizer coated with an NBPT solution containing 50.0% PG, 30.0% DMSO, and 20.0% NBPT by weight. The testing was conducted for 7 days at 22° C. using a commercially available potting soil blend, and was analyzed using a chemiluminescence ammonia analyzer.

Commercial granulated urea was treated with the NBPT solution of example 1. Both untreated and treated urea were applied to a commercially available potting soil blend at 22° C., and ammonia concentrations in the headspace were measured for a 7-day period using a chemiluminescence analyzer. Ammonia concentrations in the treated urea were considerably less than those in the untreated urea. FIG. 10 shows the results of the ammonia emissions testing.

This test shows that NBPT formulations containing DMSO are effective at reducing the hydrolysis of urea to ammonium, thereby reducing ammonia losses to the atmosphere and making the fertilizer more effective.

In certain embodiments, the present invention relates to formulations, fertilizer additives, methods and processes of making and using these formulations and/or fertilizer additives.

In an embodiment, the present invention relates to a formulation comprising N-(n-butyl) thiophosphoric triamide and one or more of an $C_{1-6}$alkylene carbonate and $R_1S(O)xR_2$ wherein $R_1$ and $R_2$ are each independently a $C_{1-6}$ alkylene group, an aryl group, or $C_{1-3}$alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Se, Te, N, and P in the ring and x is 1 or 2. In a variation, the atoms in the ring may optionally include O, S, N and P or alternatively, O, S, and N.

In one embodiment, the formulation contains $R_1S(O)xR_2$, which is dimethyl sulfoxide. Alternatively, the formulation contains $R_1S(O)xR_2$, which is a dialkyl, diaryl, or alkylaryl sulfoxide. Alternatively, $R_1$ and $R_2$ may be the same or different and each of $R_1$ and $R_2$ may be $C_{1-6}$ alkylene group, an aryl group, or $C_{1-3}$alkylenearyl group.

In an embodiment, $R_1$ is methyl, ethyl, n-propyl, phenyl or benzyl and $R_2$ is methyl, ethyl, n-propyl, phenyl or benzyl or mixtures thereof. In another embodiment, $R_1S(O)xR_2$ is sulfolane.

In an embodiment, the formulation may contain akylene carbonate, which is ethylene carbonate, propylene carbonate, butylene carbonate or mixtures thereof. In a variation, the formulation may contain akylene carbonate, which is ethylene carbonate, propylene carbonate, or mixtures thereof.

In an embodiment, the formulation may further comprise an alcohol or polyol wherein the polyol is alkylene or poly(alkylene) glycols or mixtures thereof. In an embodiment, the polyol is an alkylene glycol selected from the group consisting of ethylene, propylene, and butylene glycol, or mixtures thereof. In an embodiment, the polyol is glycerin.

In an embodiment, the formulation may further comprise an alkanolamine selected from the group consisting of ethanolamine, diethanolamine, dipropanolamine, methyl diethanolamine, monoisopropanolamine and triethanolamine.

The formulation(s) may contain an aqueous ethanolamine borate such as ARBORITE Binder. In one embodiment, the concentration of the secondary or tertiary amino alcohol may be kept above about 12% and alternatively, above about 20%. When the concentration of aqueous ethanolamine borate is below about a 12% concentration, a suspension of NBPT in the aqueous mixture may form which can be solved by agitation to be used to prepare other products.

In an embodiment of the invention, NBPT may be dissolved by melting the compound with sufficient triethanolamine to provide a mixture with up to about 30% by weight of NBPT. The resulting NBPT mixture in triethanolamine can be used to treat urea as described herein.

In another embodiment of the invention, NBPT is dissolved in diethanolamine in an amount up to 40% by weight by melting the solid into diethanolamine until a solution is obtained. The NBPT diethanolamine mixture may be used to treat urea as described herein.

In another embodiment of the invention, a liquid mixture of diisopropanolamine may be prepared by gently warming the solid until it has liquefied and the mixing NBPT with the solid up to the solubility limit. The liquid NBPT containing mixture in disioproanolamine may be used to treat urea as described herein.

In a variation, the formulation may further comprise ethyl, propyl, or butyl lactate.

In an embodiment, the N-(n-butyl)-thiophosphoric triamide (NBPT) may be present in an amount that is between about 5-75 wt. % of the formulation. In a variation, the formulation may contain between about 10 and 75 wt. % NBPT, 10 and 50 wt. % DMSO, and 10 and 80 wt. % PG (poly glycol) or alkylene carbonate. In a variation, the formulation may contain between about 10 and 60 wt. % NBPT, 10 and 40 wt. % DMSO, and 10 and 60 wt. % PG or alkylene carbonate. In a variation, the formulation may contain between about 10 and 50 wt. % NBPT, 10 and 50 wt. % DMSO, and 10 and 50 wt. % PG or alkylene carbonate. In a variation, the formulation may contain between about 10 and 40 wt. % NBPT, 10 and 40 wt. % DMSO, and 10 and 50 wt. % PG or alkylene carbonate. In a variation, the formulation may contain between about 20 and 50 wt. % NBPT, 20 and 50 wt. % DMSO, and 10 and 50 wt. % PG or alkylene carbonate. In a variation, the formulation may be diluted with water.

In an embodiment, the present invention relates to a fertilizer additive comprising N-(n-butyl) thiophosphoric triamide and one or more of an $C_{1-6}$alkylene carbonate and $R_1S(O)xR_2$ wherein $R_1$ and $R_2$ are each independently a $C_{1-6}$ alkylene group, an aryl group, or $C_{1-3}$alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Se, Te, N, and P in the ring and x is 1 or 2.

In an embodiment, the fertilizer additive may comprise N-(n-butyl)-thiophosphoric triamide and dimethyl sulfoxide. In a variation, the fertilizer may further comprise polyalkylene glycols. In a variation, the polyalkylene glycols are selected from the group consisting of polymethylene glycols, polyethylene glycols, polypropylene glycols, polybutylene glycols, and mixtures thereof.

In an embodiment, the fertilizer additive may be any of the embodiments discussed above as it relates to the formulation.

In an embodiment, the present invention relates to a method of reducing the volatility of urea fertilizers comprising adding a composition that comprises N-(n-butyl)-thiophosphoric triamide and one or more of an $C_{1-6}$alkylene carbonate and $R_1S(O)xR_2$ wherein $R_1$ and $R_2$ are each independently a $C_{1-6}$ alkylene group, an aryl group, or $C_{1-3}$alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Se, Te, N, and P in the ring and x is 1 or 2.

In an embodiment, the present invention relates to a method of making a formulation and/or fertilizer additive, wherein to N-(n-butyl)-thiophosphoric triamide is added one or more of an $C_{1-6}$alkylene carbonate and $R_1S(O)xR_2$ wherein $R_1$ and $R_2$ are each independently a $C_{1-6}$ alkylene group, an aryl group, or $C_{1-3}$alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of 0, S, Se, Te, N, and P in the ring and x is 1 or 2.

In an embodiment, the methods may comprise $R_1S(O)xR_2$, which is dimethyl sulfoxide.

In an embodiment, the methods may comprise $C_{1-6}$alkylene carbonate, which is ethylene carbonate, propylene carbonate, butylene carbonate or mixtures thereof.

In an embodiment, the methods may comprise any of the formulations and/or fertilizer additives discussed above.

Every patent mentioned herein is incorporated by reference in its entirety.

It should be understood that the present invention is not to be limited by the above description. Modifications can be made to the above without departing from the spirit and scope of the invention. It is contemplated and therefore within the scope of the present invention that any feature that is described above can be combined with any other feature that is described above. Moreover, it should be understood that the present invention contemplates minor modifications that can be made to the formulations, compositions, fertilizer additives and methods of the present invention. When ranges are discussed, any number that may not be explicitly disclosed but fits within the range is contemplated as an endpoint for the range. The scope of protection to be afforded is to be determined by the claims which follow and the breadth of interpretation which the law allows.

What is claimed is:

1. A fertilizer composition comprising
 a. granular urea,
 b. one or more phosphoramides, wherein the one or more phosphoramides are selected from the group consisting of aliphatic phosphoric triamides and N-alkyl thiophosphoric triamides,
 c. one or more aprotic solvents wherein said one or more aprotic solvents comprise dimethyl sulfoxide,
 d. dyes/colorants, and
 e. optionally one or more members selected from the group consisting of i) urea formaldehyde polymers and ii) dicyandiamide.

2. The composition of claim 1, wherein the one or more phosphoramides comprise N-(n-butyl) thiophosphoric triamide.

3. The composition of claim/wherein the weight percent of N-(n-butyl) thiophosphoric triamide comprises 5-58.9% relative to dimethyl sulfoxide.

4. The composition of claim 1, wherein said composition further comprises one or more members selected from the group consisting of a) one or more $C_1$ to $C_6$ alcohols, b) one or more polyols selected from the group consisting of alkylene and poly(alkylene) glycols, wherein the one or more alkylene glycols are selected from the group consisting of ethylene glycol, propylene glycol, and butylene glycol and wherein the one or more poly(alkylene) glycols are selected from the group consisting of polymethylene glycols, polyethylene glycols, polypropylene glycols, and polybutylene glycols c) glycerin, and d) one or more alkyl lactates selected from the group consisting of ethyl lactate, propyl lactate, and butyl lactate.

5. The composition of claim 4, wherein the one or more protic solvents comprise one or more poly(alkylene) glycols are selected from the group consisting of polymethylene glycols, polyethylene glycols, polypropylene glycols, and polybutylene glycols.

6. The composition of claim 5, wherein the one or more poly(alkylene) glycols comprise polyethylene glycols.

7. The composition of claim 1, wherein the composition further comprises one or more additional aprotic solvents selected from the group consisting of a) one or more alkylene carbonates selected from the group consisting of propylene carbonate, ethylene carbonate, and butylene carbonate, b) 2-methoxyethyl ether, c) cyclohexylpyrrolidone, d) 1,3 dimethyl-2-imidazolidinone, e) dimethyloxyethane, and f) the organo phosphorous liquid hexamethyl phosphoramide.

8. The composition of claim 1, wherein the composition further comprises one or more members selected from the group consisting of buffers, flow aids, silicas, and surfactants.

9. The composition of claim 1 wherein the dyes/colorants provide a visual confirmation that said phosphoramides have been delivered as an even coating on the granular urea.

10. The composition of claim 1, wherein the composition further comprises water.

11. A fertilizer composition comprising
 a. granular urea,
 b. one or more phosphoramides,
 c. one or more polar aprotic solvents selected from the group consisting of
  i. dimethyl sulfoxide, and
  ii. one or more members selected from the group consisting of dialkyl, diaryl, or alkylaryl sulfoxide(s) selected from the formula structure

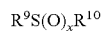

wherein
   $R^9$ and $R^{10}$ are each independently a $C_1$-$C_6$ alkylene group, an aryl group or $C_1$-$C_3$ alkylenearyl group, or $R^9$ and $R^{10}$ with the sulfur to which they are attached form a 4 to 8 membered ring wherein $R^9$ and $R^{10}$ together are a $C_1$-$C_6$ alkylene group which optionally contains one or more atoms selected from the group consisting of O, S, Se, Te, N, and P in the ring, and
   x=1 or 2,
 d. one or more solvents selected from the group consisting of one or more additional aprotic solvents and one or more protic solvents and
 e. optionally one or more members selected from the group consisting of urea formaldehyde polymers and dicyandiamide and
 wherein the one or more phosphoramides are selected from the group consisting of aliphatic phosphoric triamides and N-alkyl thiophosphoric triamides.

12. The composition of claim 11, wherein the one or more phosphoramides comprise N-(n-butyl) thiophosphoric triamide and the weight percent of N-(n-butyl) thiophosphoric triamide comprises 5-75% relative to said one or more polar aprotic solvents and said one or more solvents.

13. The composition of claim 11, wherein the composition comprises the polar aprotic solvent dimethyl sulfoxide.

14. The composition of claim 11, wherein the one or more protic solvents selected are from the group consisting of a) one or more $C_1$ to $C_6$ alcohols, b) one or more polyols selected from the group consisting of alkylene and poly (alkylene) glycols, wherein the one or more alkylene glycols are selected from the group consisting of ethylene glycol, propylene glycol, and butylene glycol and wherein one or more poly(alkylene) glycols are selected from the group consisting of polymethylene glycols, polyethylene glycols, polypropylene glycols, and polybutylene glycols c) glycerin, d) one or more alkyl lactates selected from the group consisting of ethyl lactate, propyl lactate, and butyl lactate, and e) one or more alkanolamines selected from the group consisting of ethanolamine, diethanolamine, dipropanolamine, methyl diethanolamine, monoisopropanolamine, and triethanolamine.

15. The composition of claim 14, wherein the one or more protic solvents comprise polyethylene glycols.

16. The composition of claim 11, wherein the one or more additional aprotic solvents are selected from the group consisting of a) one or more alkylene carbonates selected from the group consisting of propylene carbonate, ethylene carbonate, and butylene carbonate, b) 2-methoxyethyl ether, c) cyclohexylpyrrolidone, d) 1,3 dimethyl-2-imidazolidinone, and e) organo 17 phosphorous liquid hexamethyl phosphoramides.

17. The composition of claim 11, wherein the composition further comprises one or more members selected from the group consisting of dyes/colorants, buffers, flow aids, silicas, and surfactants.

18. The composition of claim 17 wherein the dyes/colorants provide a visual confirmation that said phosphoramides have been delivered as an even coating on the granular urea.

19. The composition of claim 11, wherein the composition further comprises water.

20. A fertilizer composition comprising
 a. granular urea,
 b. one or more phosphoramides, wherein the one or more phosphoramides comprise N-(n-butyl) thiophosphoric triamide,
 c. one or more aprotic solvents wherein said one or more aprotic solvents comprise dimethyl sulfoxide,
 d. polyethylene glycols, and
 e. optionally one or more members selected from the group consisting of i) urea formaldehyde polymers and ii) dicyandiamide,
 wherein the compositional weight percent of N-(n-butyl) thiophosphoric triamide comprises 5-75% relative to the dimethyl sulfoxide and polyethylene glycols.

* * * * *